(12) United States Patent
Umezu et al.

(10) Patent No.: US 8,603,162 B2
(45) Date of Patent: Dec. 10, 2013

(54) STENTLESS ARTIFICIAL MITRAL VALVE

(75) Inventors: Mitsuo Umezu, Totsuka-machi (JP); Hitoshi Kasegawa, Totsuka-machi (JP)

(73) Assignee: Waseda University, Tokyo (JP)

( * ) Notice: Subject to any disclaimer, the term of this patent is extended or adjusted under 35 U.S.C. 154(b) by 0 days.

(21) Appl. No.: 13/177,183

(22) Filed: Jul. 6, 2011

(65) Prior Publication Data

US 2013/0013058 A1 Jan. 10, 2013

(51) Int. Cl.
*A61F 2/24* (2006.01)
(52) U.S. Cl.
USPC ........................................ 623/2.12; 623/1.26
(58) Field of Classification Search
USPC .............................. 623/1.24, 1.26, 2.12–2.19
See application file for complete search history.

(56) References Cited

U.S. PATENT DOCUMENTS

| | | | | |
|---|---|---|---|---|
| 6,129,758 A * | 10/2000 | Love | ............................ | 623/2.11 |
| 6,454,799 B1 * | 9/2002 | Schreck | ........................ | 623/2.18 |
| 6,461,382 B1 * | 10/2002 | Cao | ................................ | 623/2.19 |
| 6,491,511 B1 * | 12/2002 | Duran et al. | ................... | 425/394 |
| 6,605,112 B1 * | 8/2003 | Moll et al. | .................... | 623/1.24 |
| 6,685,739 B2 * | 2/2004 | DiMatteo et al. | ............ | 623/1.24 |
| 7,455,689 B2 * | 11/2008 | Johnson | ........................ | 623/2.18 |
| 7,914,569 B2 * | 3/2011 | Nguyen et al. | ................ | 623/1.18 |
| 2002/0052651 A1 * | 5/2002 | Myers et al. | .................. | 623/2.15 |
| 2003/0229394 A1 * | 12/2003 | Ogle et al. | .................... | 623/2.14 |
| 2004/0122512 A1 * | 6/2004 | Navia et al. | ................... | 623/2.12 |

FOREIGN PATENT DOCUMENTS

| | | |
|---|---|---|
| JP | 2010-148633 A | 7/2010 |
| WO | WO2005/067821 A1 | 7/2005 |

* cited by examiner

*Primary Examiner* — Paul Prebilic
(74) *Attorney, Agent, or Firm* — Westerman, Hattori, Daniels & Adrian, LLP

(57) ABSTRACT

An artificial mitral valve has a ring, an anterior cusp-side region, a posterior cusp-side region and a valve leaflet connected along an outer edge of the ring. The valve leaflet includes an anterior cusp forming member connected to the anterior cusp-side region and a posterior cusp forming member connected to the posterior cusp-side region. The anterior cusp forming member has an upper edge joined to the ring and a lower edge that forms a bifurcated portion. The upper edge is made up of a pair of right and left edges that incline inward and upward from the right and left sides, and a curved edge interposed between the inclined edges that curves along the anterior cusp-side region. The posterior cusp forming member has an upper edge joined to the ring and a lower edge that forms a bifurcated portion.

1 Claim, 5 Drawing Sheets

FIG.5
(A)
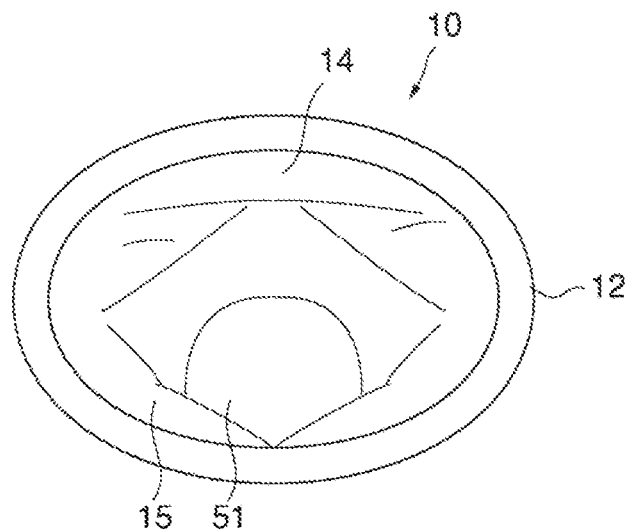
(B)
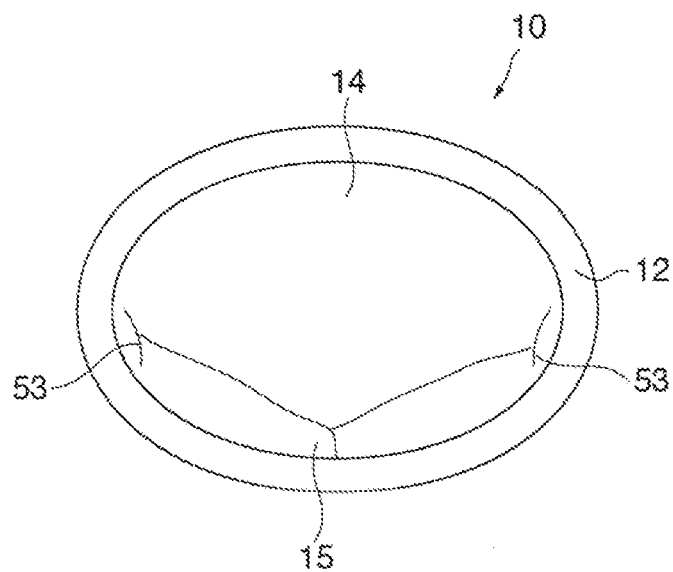

STENTLESS ARTIFICIAL MITRAL VALVE

BACKGROUND OF THE INVENTION

1. Field of the Invention

The present invention relates to a stentless artificial mitral valve and artificial valve leaflet, and template and cutter for forming the artificial valve leaflet, and more particularly, to a stentless artificial mitral valve, and artificial valve leaflet which are implanted into the heart on the occasion of valve replacement for valvular disease of heart or the like, capable of realizing valve behavior similar to a real mitral valve.

2. Description of the Related Art

Of the human heart valves, the mitral valve is a unidirectional valve located between the left atrium into which the blood from the lung flows and the left ventricle that sends out the blood flown into the left atrium to the whole body, made up of two valve leaflets called ""anterior cusp"" and ""posterior cusp,"" and is different in structure from other heart valves such as the aortic valve made up of three valve leaflets. The anterior cusp and posterior cusp of the mitral valve are located within an annular portion called ""valve annulus"" and connected to the wall of the left ventricle via a string-like tendinous cord. Here, the interior of the left ventricle is held in a positive pressure state in a contraction phase of the heart and the anterior cusp and posterior cusp come into close contact, producing a closed valve state, whereas in a diastolic phase of the heart, the interior of the left ventricle is held in a negative pressure state and the anterior cusp and posterior cusp are mutually pulled, producing an open valve state.

One of remedies for a patient suffering from mitral regurgitation with the mitral valve disabled by a lesion and the blood flowing backward from the left ventricle to the left atrium is artificial valve replacement whereby the lesioned mitral valve is removed and replaced by an artificial valve.

A so-called prosthetic valve is known as such an artificial valve formed using a biological tissue of swine or the like and International Publication No. WO2005-067821 discloses two artificial valves made up of a biological tissue. The document discloses two types of artificial valve; a stent artificial valve having a frame called ""stent"" and a stentless artificial valve with no stent. The former stent artificial valve is constructed of a stent made of a wire and constituting the outside shape of the artificial valve, and first and second valve leaflets joined to the stent. Here, the first and second valve leaflets are provided so as to be cloak-shaped when planar expanded and is formed of a biological tissue resected from the aortic valve of swine. On the other hand, the latter stentless artificial valve is created by sewing the first and second valve leaflets to the inner surface of a tubular body made up of a biological tissue.

SUMMARY OF THE INVENTION

However, since the stent artificial valve deteriorates and alters with time, the artificial valve needs to be replaced at a relatively short period, resulting in a problem that it is difficult to use the stent artificial valve for juvenile patients for whom the number of replacements throughout the lifetime increases. That is, since the first and second valve leaflets are joined to the stent in a complicated manner, mechanical stress caused by the opening/closing movement of the valve applies to the joints, which produces functional deterioration with time. The mitral valve region in particular has large mechanical stress when the valve is closed compared to the aortic valve region or the like and the aforementioned deterioration or alteration advances rapidly. Furthermore, although the mitral valve is connected to the papillary muscle via the tendinous cord, when the mitral valve is replaced by the artificial valve, part of the papillary muscle which forms part of the wall of the left ventricle is removed and the replacing artificial valve is then sewn only to the periphery of the valve annulus of the heart. For this reason, after the valve replacement, the part of the papillary muscle remains to be resected, the strength of the wall of the left ventricle becomes smaller than before the surgery, which may produce deterioration the left heart function. Furthermore, when manufacturing the stent artificial valve, the sheet-like first and second valve leaflets need to be joined to the surface of the stent which is three-dimensionally structured with wires in a complicated manner, which not only complicates the manufacturing process of the artificial valve but also requires fine positional adjustment when the first and second valve leaflets are joined so as to realize desired valve opening/closing movement, resulting in another problem that the artificial valve cannot be easily manufactured.

On the other hand, since the aforementioned stentless artificial valve has a rectilinear tubular outside shape, it is hard to be implanted into the heart, high-level manipulation is required for the medical doctor and application to infant patients having small-sized hearts is particularly difficult. Furthermore, as in the case of the stent artificial valve, this stentless artificial valve may cause deterioration of the left heart functions after valve replacement. Moreover, when manufacturing the stentless artificial valve, it is necessary to join the first and second valve leaflets to the inner surface of the rectilinear tube while performing fine positional adjustment so as to realize the desired valve opening/closing movement, resulting in a problem that the joining operation becomes more difficult than the stent artificial valve and the manufacturing process of the artificial valve becomes still more complicated.

The present invention has been implemented in view of such problems and it is an object of the present invention to provide a stentless artificial mitral valve and artificial valve leaflets that can realize valve behavior similar to a real one without using any stent, from which suppression of deterioration of cardiac functions after valve replacement can be expected.

Furthermore, it is another object of the present invention to provide a stentless artificial mitral valve which can be implanted into the heart relatively easily, which has a simple configuration and easy to manufacture.

Furthermore, it is a further object of the present invention to provide a template and cutter that can easily form the artificial valve leaflets.

In order to attain the above objects, the present invention adopts a configuration of a stentless artificial mitral valve provided with a ring and artificial valve leaflets connected along an outer edge of the ring, wherein the ring is divided along the circumferential direction into two; an anterior cusp-side region and a posterior cusp-side region, the artificial valve leaflet includes anterior cusp forming member connected to the anterior cusp-side region and symmetric posterior cusp forming member connected to the posterior cusp-side region, the anterior cusp forming member includes an upper edge joined to the ring and a lower edge connected to the upper edge and forming a bifurcated portion which is open downward, the upper edge is made up of a pair of right and left inclined edges inclined inward and upward from right and left ends and a curved edge interposed between the inclined edges and having a curved shape of part of the anterior cusp-side region and the posterior cusp forming member includes an upper edge joined to the ring and a lower edge connected to the upper edge and forming a bifurcated portion which is open downward.

Furthermore, the present invention also provides an artificial valve leaflet implanted into the heart and functioning as an artificial valve, which adopts a configuration including an anterior cusp forming member and a posterior cusp forming member, wherein the anterior cusp forming member includes an upper edge sewn to a valve annulus of the heart and a lower edge connected to the upper edge and forming a bifurcated portion which is open downward, the upper edge is made up of a pair of right and left inclined edges inclined inward and upward from right and left ends and a curved edge interposed between the inclined edges and having a curved shape, and the posterior cusp forming member includes an upper edge sewn to the valve annulus and a lower edge connected to the upper edge and forming a bifurcated portion which is open downward.

Furthermore, the present invention also provides a template for forming the artificial valve leaflet, which adopts a configuration including an anterior cusp hole having an inner edge portion corresponding to an outside shape of the anterior cusp forming member and a posterior cusp hole having an inner edge portion corresponding to an outside shape of the posterior cusp forming member.

Furthermore, the present invention also provides a cutter for forming the artificial valve leaflet, which adopts a configuration including a blade portion having a shape corresponding to the outside shape of the anterior cusp forming member and/or the outside shape of the posterior cusp forming member.

It should be noted that "up," "down," "left" and "right" used for the artificial valve leaflet in the scope of claims and the present description correspond to "up," "down," "left" and "right" in FIG. 2 unless specified otherwise.

The present invention is formed without using any stent and is therefore free of mechanical stress caused by the presence of the stent and can suppress deterioration or alteration of the artificial valve with time compared to a stent artificial valve. Furthermore, as will be described later, experiments by the present inventor et al. have proven that when placed under beating heart similar to the real heart, the present invention demonstrates valve behavior or blood flow extremely similar to the human mitral valve. Furthermore, by sewing the respective bifurcated portions of the anterior cusp forming member and posterior cusp forming member to the papillary muscle of the heart, the bifurcated portions function as the tendinous cords present before valve replacement. It can be expected to reinforce the partially removed papillary muscle and prevent deterioration of left heart function caused by resecting the mitral valve.

Furthermore, the stentless artificial mitral valve of the present invention can be implanted into the heart by only sewing the ring to the valve annulus of the heart and sewing the bifurcated portion to the papillary muscle, and it is thereby possible to realize the implantation extremely easily and the present invention is easily applicable to infants or the like having small-sized hearts. Moreover, the stentless artificial mitral valve has a simple configuration and it is only necessary to join the artificial valve leaflet along the outer edge of the ring when manufacturing the artificial valve, which eliminates the necessity of fine adjustment or complicated connections or the like required in the conventional artificial valve and simplifies manufacturing.

Furthermore, use of the template of the present invention allows the artificial valve leaflet to be formed easily.

BRIEF DESCRIPTION OF THE DRAWINGS

FIG. 5(A) is a schematic plan view describing valve behavior of the stentless artificial mitral valve in a diastolic phase and FIG. 5(B) is likewise a schematic plan view describing the valve behavior in a contraction phase.

DETAILED DESCRIPTION OF THE PREFERRED EMBODIMENT

Hereinafter, an embodiment of the present invention will be described with reference to the accompanying drawings.

Figure 1:
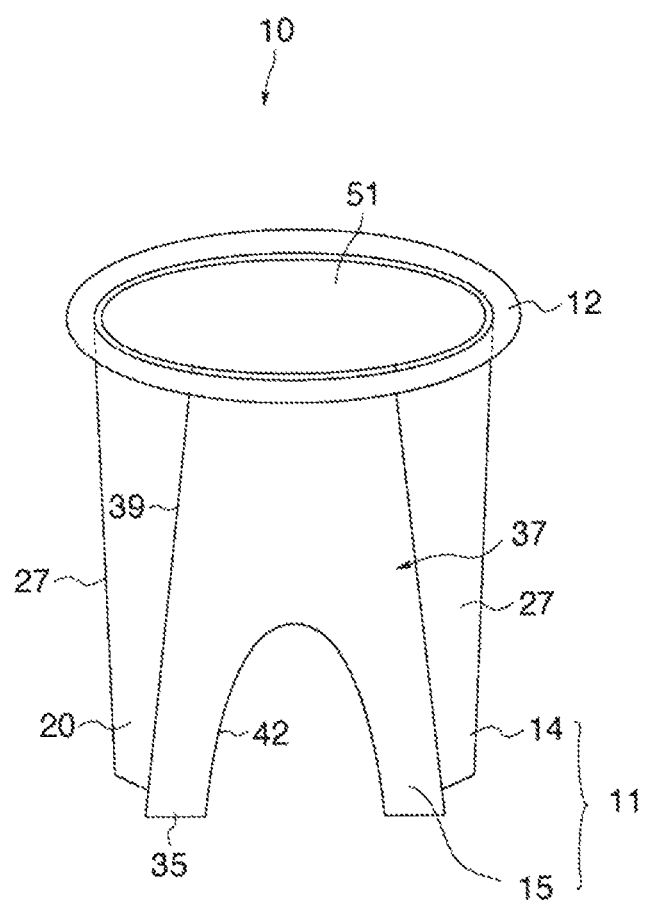
FIG. 1 is a schematic perspective view of a stentless artificial mitral valve according to the present embodiment.
Figure 2:
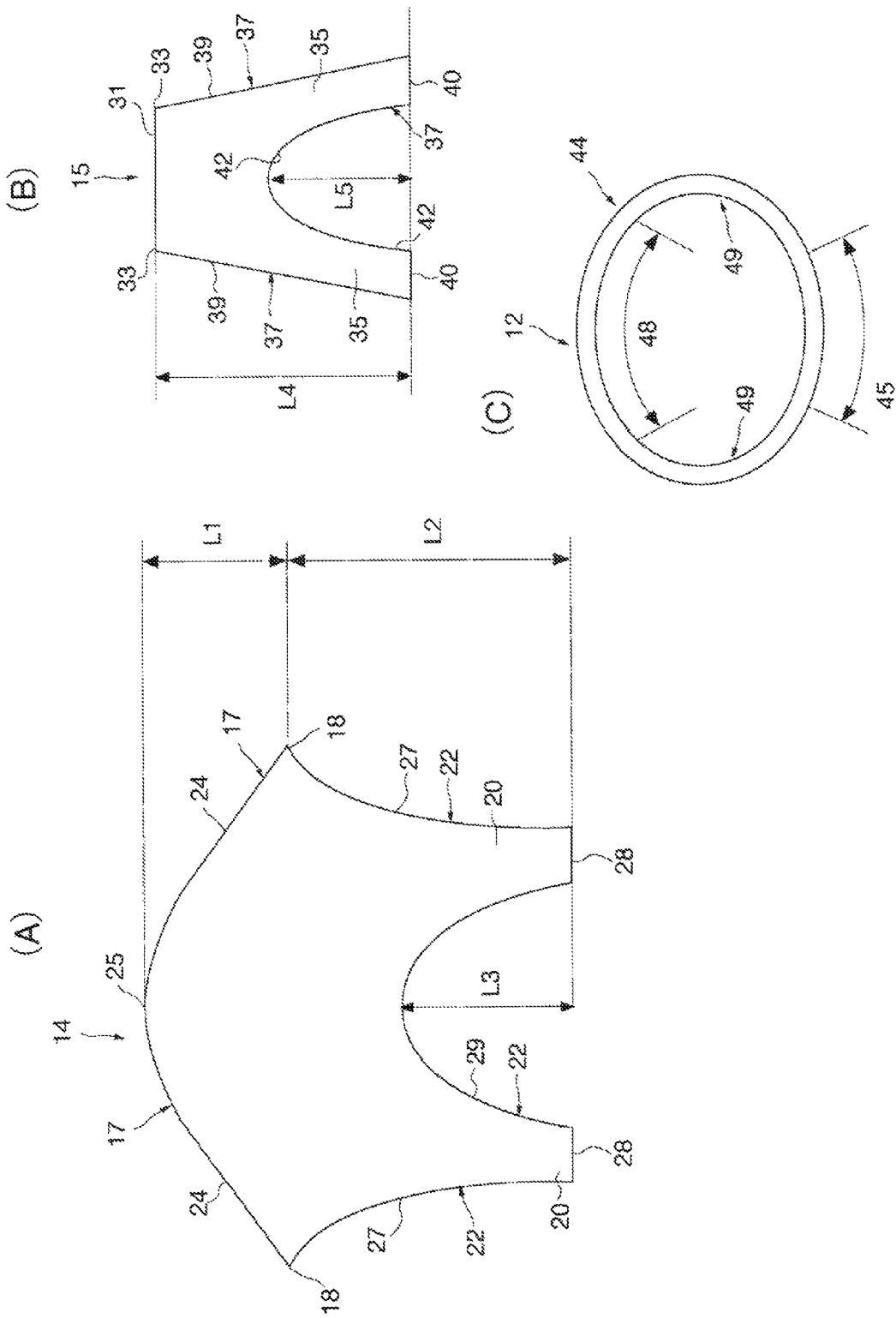
FIG. 2(A) is a schematic development view of the anterior cusp forming member.
FIG. 2(B) is a schematic development view of the posterior cusp forming member and FIG. 2(C) is a schematic plan view of the ring.

FIG. 1 shows a schematic perspective view of a stentless artificial mitral valve according to the present embodiment and FIG. 2 shows a schematic plan view of components of the stentless artificial mitral valve. In these FIGS, a stentless artificial mitral valve 10 is an artificial mitral valve capable of realizing valve behavior substantially equivalent to that of the mitral valve of the human body and has a bicuspidal valve structure made up of two valve leaflets. The stentless artificial mitral valve 10 is configured by including an artificial valve leaflet 11 having a shape corresponding to the anterior cusp and the posterior cusp of the mitral valve, and a ring 12 that supports the artificial valve leaflet 11.

The artificial valve leaflet 11 is made up of an anterior cusp forming member 14 and a posterior cusp forming member 15, which are each symmetric sheet-like members. The artificial valve leaflet 11 can be formed of a self-tissue such as pericardium of a patient himself/herself, biological material such as pericardium picked from animal such as bovine subjected to fixing treatment with glutalaldehyde or artificial material such as latex having biocompatibility.

As shown in FIG. 2, the anterior cusp forming member 14 is made up of an upper edge 17 constituting a top end portion thereof, boundary portions 18, 18 on the right and left sides at the bottom of the upper edge 17 and a lower edge 22 connected to the boundary portions 18, 18 and forming a bifurcated portion 20 which is open downward.

The upper edge 17 is made up of a pair of right and left inclined edges 24, 24 inclined inward and upward from the boundary portions 18, 18 at the right and left ends of the lower edge 22 and a curved edge 25 connected to the inclined edges 24, 24 and located at substantially the center in the horizontal direction. The inclined edges 24, 24 extend substantially rectilinearly between the boundary portions 18, 18 and the end of the curved edge 25. The curved edge 25 has a curved shape having substantially the same curvature as a reference region 48 which forms part of an anterior cusp-side region 44 of the ring 12, which will be described later.

The lower edge 22 is made up of semi-parabolic side edges 27, 27 which extend inward and downward from the boundary portions 18, 18 on the right and left sides, horizontal edges 28, 28 which extend inward in the horizontal direction from the bottom of the side edges 27, 27 and a parabolic center edge 29 which extends upward from the inner ends of the horizontal edges 28, 28.

A maximum height L1 of the upper edge 17 from the boundary portions 18 is set to be smaller than a maximum height L2 of the lower edge 22.

Furthermore, a recess distance L3 in the vertical direction of the center edge 29 is set to be smaller than the maximum height L2.

The posterior cusp forming member 15 as a whole is provided in a size smaller than the anterior cusp forming member 14 and is made up of an upper edge 31 that extends substantially horizontally, boundary portions 33, 33 located on the right and left sides of the upper edge 31 and a lower edge 37 connected to the boundary portions 33, 33 and forming a bifurcated portion 35 which is open downward.

The lower edge 37 is made up of side edges 39, 39 that extend downward rectilinearly so as to gradually expand outward from the boundary portions 33, 33, horizontal edges 40, 40 that extend inward substantially horizontally from the bottom of the side edges 39, 39 and a parabolic center edge 42 that extends upward from the inner ends of the horizontal edges 40, 40.

A height L4 of the side edges 39, 39 is set to be greater than a recess distance L5 of the center edge 42 in the vertical direction.

The ring 12 has a substantially ellipsoidal shape in a plan view and is elastically deformable. This ring 12 is divided along the circumferential direction into two; an anterior cusp-side region 44 and a posterior cusp-side region 45.

The anterior cusp-side region 44 is designed so that the upper edge 17 of the anterior cusp forming member 14 is joined to the inner circumferential edge thereof and is divided into two; a reference region 48 to which the curved edge 25 is joined and remaining regions 49, 49 which are located on the right and left sides of the reference region 48 and to which the inclined edges 24, 24 are joined. The reference region 48 is not particularly limited, but is provided so as to have a circumferential length on the order of approximately ⅓ of the whole circumferential length of the ring 12. Furthermore, the remaining regions 49, 49 are provided so as to have a circumferential length shorter than the length of the inclined edges 24, 24 and designed such that when the inclined edges 24, 24 are joined to the remaining regions 49, 49, a certain degree of slackness and crease are produced on the surface of the anterior cusp forming member 14 in the vicinity thereof.

The posterior cusp-side region 45 is set at a position opposed to the reference region 48 so that the upper edge 31 of the posterior cusp forming member 15 is joined thereto. The posterior cusp-side region 45 is shorter than the circumferential length of the reference region 48 and provided so as to have a circumferential length that allows the posterior cusp forming member 15 to be joined with substantially no slackness.

As the ring 12, various types of ring conventionally used as an artificial valve annulus can be adopted, in short, any ring formed of a material having biocompatibility can be used.

Next, a manufacturing procedure for the stentless artificial valve 10 will be described.

Figure 3:
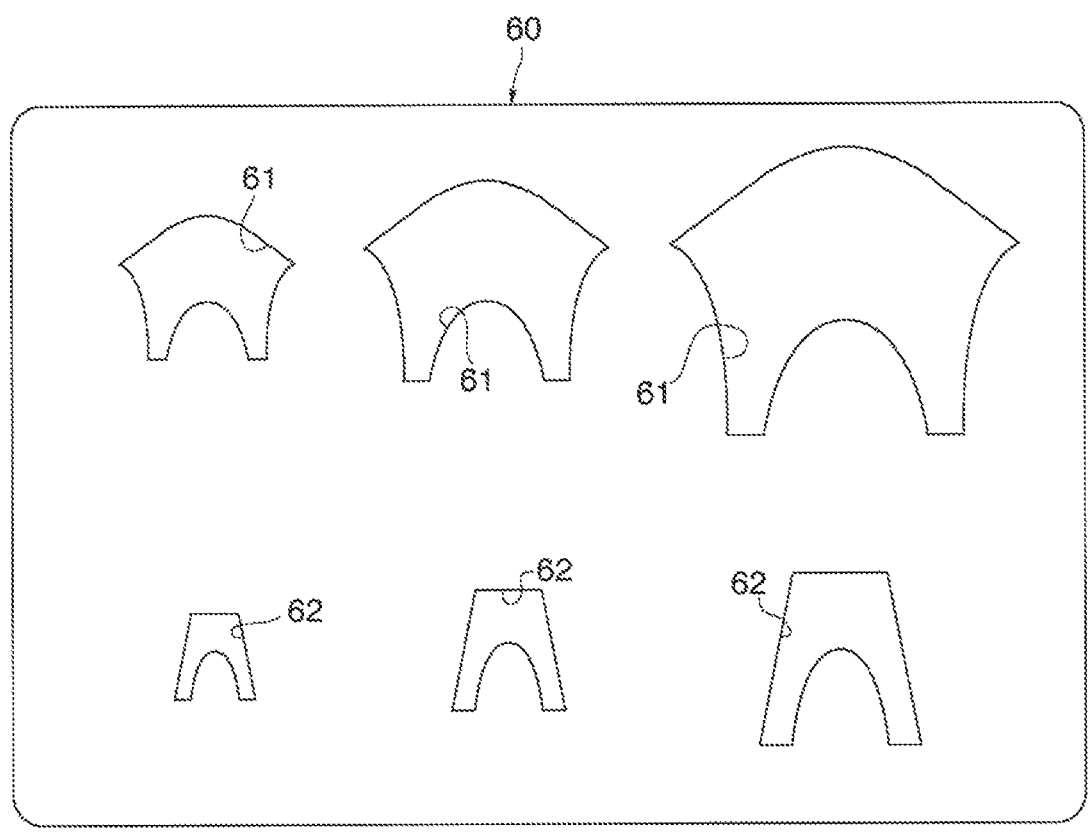
FIG. 3 is a schematic plan view of template for forming the artificial valve leaflet.

First, a sheet member made of the aforementioned biological material, self-tissue such as the pericardium of the patient or biocompatible artificial material is provided, a template 60 shown in FIG. 3 is used, the anterior cusp forming member 14 and the posterior cusp forming member 15 are formed from the sheet member. The template 60 is provided with an anterior cusp hole 61 having an inner edge portion corresponding to the outside shape of the anterior cusp forming member 14 and a posterior cusp hole 62 having an inner edge portion corresponding to the outside shape of the posterior cusp forming member 15. The template 60 is provided with a plurality of the anterior cusp holes 61 and the posterior cusp holes 62 having similar shapes and different sizes. Therefore, the anterior cusp forming member 14 and posterior cusp forming member 15 of the aforementioned shape are obtained by selecting an anterior cusp hole 61 and a posterior cusp hole 62 in a size suitable for the patient as the implantation target, placing the selected holes 61 and 62 on the sheet member and removing the sheet member along the inner edge portions of the holes 61 and 62 using a cutter (not shown). Though not shown, it is also possible to form the anterior cusp forming member 14 and the posterior cusp forming member 15 by punching out the sheet member into shapes corresponding to the outside shapes of the anterior cusp forming member 14 and the posterior cusp forming member 15 using a cutter provided with a blade portion in a shape corresponding to the outside shape of the anterior cusp forming member 14 and the posterior cusp forming member 15.

Figure 4:
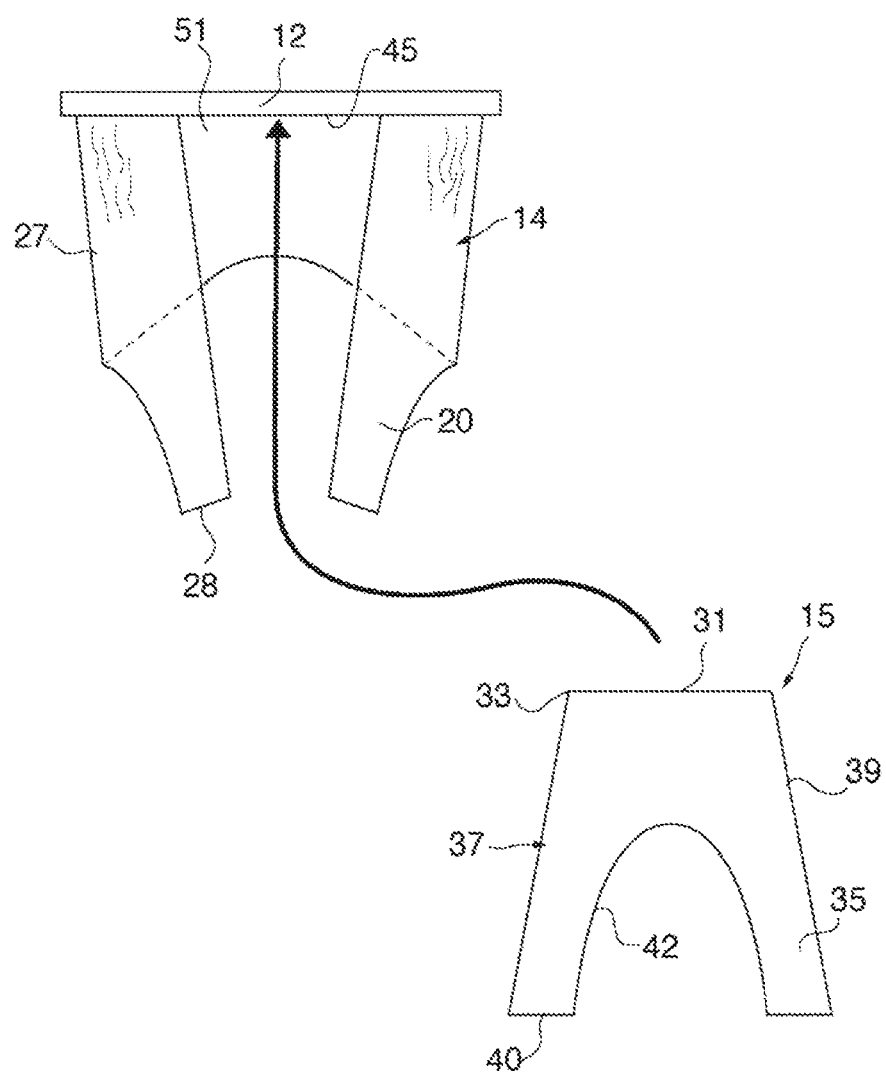
FIG. 4 is a partially exploded front view for illustrating an assembly procedure for the stentless artificial mitral valve.

Next, as shown in FIG. 4, the anterior cusp forming member 14 is joined to the ring 12. Here, the curved edge 25 of substantially the same curvature as the reference region 48 is sewn to the inner circumferential edge of the reference region 48 (see FIG. 2) of the ring 12 with string and then the inclined edges 24, 24 are sewn to the inner circumferential edges of the remaining regions 49, 49 with string. The upper edge 31 of the posterior cusp forming member 15 is then sewn to the inner circumferential edge of the posterior cusp-side region 45 of the ring 12 with string. In this condition, the anterior cusp forming member 14 and the posterior cusp forming member 15 are joined to the ring 12 in the circumferential direction with substantially no gap and crease caused by slackness appears on the surface of the anterior cusp forming member 14 in the vicinity of the remaining regions 49, 49.

In this assembly state, the anterior cusp forming member 14 and the posterior cusp forming member 15 are suspended downward from the inner circumferential edge of the ring 12, and the inside of the ring 12 constitutes a blood channel 51.

In the aforementioned stentless artificial mitral valve 10, the outer circumferential edge of the ring 12 is sewn to the valve annulus (not shown) of the heart and the bifurcated portions 20 and 35 of the anterior cusp forming member 14 and the posterior cusp forming member 15 are sewn to the papillary muscle of the left ventricle (not shown) and the stentless artificial mitral valve 10 is thereby implanted into the heart.

The stentless artificial mitral valve 10 implanted in this way behaves as follows.

In a diastolic phase of the heart, the bifurcated portions 20 and 35 are pulled downward due to a negative pressure inside the left ventricle and descent of the papillary muscle, and the channel 51 is formed inside the ring 12 as shown in FIG. 5(A). On the other hand, in a contraction phase of the heart, the surfaces of the anterior cusp forming member 14 and the posterior cusp forming member 15 suspended from the ring 12 are raised toward the ring 12 due to a positive pressure inside the left ventricle and ascent of the papillary muscle, and the channel 51 is closed with the surfaces as shown in FIG. 5(B).

Next, an experiment for proving the above described valve behavior and blood flow in the channel 51 was conducted using a mitral valve simulator (not shown) developed by the present inventor et al.

The mitral valve simulator is a publicly known apparatus for simulating the behavior of the mitral valve region and the blood flow in the heart of the human body. Here, detailed descriptions of the apparatus configuration will be omitted.

In the present experiment, the stentless artificial mitral valve 10 was set in the mitral valve simulator as in the case of implantation into the human body and the mitral valve simulator was driven. Images of the behavior of the stentless artificial mitral valve 10 were taken using a digital video camera and the flow rate or the like before and after the stentless artificial mitral valve 10 was measured. As the drive condition of the mitral valve simulator in this case, conditions corresponding to a predetermined heart condition, that is, a beating rate of 70 BPM, heart contraction factor of 35%, left ventricle positive pressure of 200 mmHg and left ventricle negative pressure of 50 mmHg were set.

Furthermore, the size of the stentless artificial valve 10 used in the present embodiment was set as follows. That is, L1=20 mm, L2=40 mm, L3=25 mm, L4=35 mm and L5=20 mm. Furthermore, the width in the horizontal direction of the anterior cusp forming member 14 was set to 75 mm and heights in the vertical direction of the inclined edges 24, 24 were set to 16 mm, the width in the horizontal direction of the horizontal edges 28, 28 was set to 7 mm and the width in the horizontal direction of the center edge 29 was set to 34 mm. Furthermore, the width in the horizontal direction of the upper edge 31 of the posterior cusp forming member 15 was set to 20 mm, the width in the horizontal direction of the horizontal edges 40, 40 was set to 7 mm and the width in the horizontal direction of the center edge 42 was set to 20 mm.

As a result of the above described experiment, the valve behavior shown in FIG. 5 was obtained. That is, as shown in FIG. 5(A), in the diastolic phase, it has been proved that the channel 51 providing a sufficient effective mitral valve area was formed, and in this case, the resistance against the flow in the channel was small and a practical flow condition was obtained. On the other hand, in the contraction phase, as shown in FIG. 5(B), the surfaces of the anterior cusp forming member 14 and the posterior cusp forming member 15 were raised, closely joined together and the channel 51 was closed. This connection state is extremely similar to the actual closure by the connection between the anterior cusp and the posterior cusp of the mitral valve and a hinge portion 53, similar to the commissure seen in the actual mitral valve, was formed.

Therefore, such an embodiment can realize valve behavior similar to that of the actual mitral valve.

Furthermore, it is possible to relatively easily implant the stentless artificial mitral valve 10 into the heart by sewing the ring 12 to the valve annulus of the heart and sewing the bifurcated portions 20 and 35 to the papillary muscle of the left ventricle, and the stentless artificial mitral valve 10 is useful in application to infants having small-sized hearts.

Furthermore, since the stentless artificial mitral valve 10 is implanted with the bifurcated portions 20 and 35 sewn to the papillary muscle, after replacement by the stentless artificial valve 10, the bifurcated portions 20 and 35 reinforce the wall of the left ventricle and the effect of suppression of deterioration of the function of the left ventricle after the surgery can be expected.

Furthermore, since the stentless artificial mitral valve 10 can be formed by only sewing the artificial valve leaflet 11 to the inner circumferential edge of the ring 12, the stentless artificial mitral valve 10 can be easily manufactured without making fine adjustment or the like.

Moreover, using a decellularized animal tissue for the artificial valve leaflet 11 can suppress calcification of the artificial valve leaflet 11 with time and further improve durability of the stentless artificial mitral valve 10.

In the present embodiment, the stentless artificial mitral valve 10 is implanted into the heart with the artificial valve leaflet 11 attached to the ring 12 beforehand, but in the present invention, it is possible to directly sew the anterior cusp forming member 14 and the posterior cusp forming member 15 to the valve annulus of the heart during the surgery without using the ring 12.

Furthermore, the stentless artificial mitral valve 10 is applicable not only to mitral valve replacement but also to other valve replacement as long as there is no hindrance.

Furthermore, the following can be illustrated as preparations for the artificial valve leaflet 11 for implantation. That is, the artificial valve leaflets 11 of various sizes are formed beforehand from the sheet member which becomes the material using the aforementioned template 60 or a cutter (not shown) and one in an appropriate size is selected at the site of surgery. Alternatively, the artificial valve leaflet 11 in a size appropriate for the patient is formed at the site of surgery using the aforementioned template 60 or cutter (not shown) from the pericardium picked from the patient during the surgery.

Besides, shapes and structures of the respective members of the present invention are not limited to those in illustrated examples, but various modifications can be made as long as substantially the same operations are obtained.

What is claimed is:

1. A stentless artificial mitral valve comprising a ring and artificial valve leaflets connected along an outer edge of the ring,
   wherein the ring is divided along the circumferential direction into two; an anterior cusp-side region and a posterior cusp-side region,
   the artificial valve leaflets comprise an anterior cusp forming member connected to the anterior cusp-side region and a posterior cusp forming member connected to the posterior cusp-side region,
   the anterior cusp forming member includes an upper edge joined to the ring and a lower edge connected to the upper edge and forming a bifurcated portion which is open downward,
   the upper edge is made up of a pair of right and left inclined edges inclined inward and upward from right and left ends and a curved edge interposed between the inclined edges and having a curved shape of part of the anterior cusp-side region, and
   the posterior cusp forming member includes an upper edge joined to the ring and a lower edge connected to the upper edge and forming a bifurcated portion which is open downward;
   wherein the bifurcated portion of the anterior cusp forming member is separate and unattached from the bifurcated portion of the posterior cusp forming member, and thus the bifurcated portions are adapted to be sewn onto native heart tissues during implantation.

* * * * *